(12) United States Patent
Neubert

(10) Patent No.: US 7,561,256 B2
(45) Date of Patent: Jul. 14, 2009

(54) METHOD AND APPARATUS FOR DETERMINING BLOOD OXYGEN

(75) Inventor: Juergen Neubert, Munich (DE)

(73) Assignee: Schwarzer GmbH, Munich (DE)

(*) Notice: Subject to any disclaimer, the term of this patent is extended or adjusted under 35 U.S.C. 154(b) by 111 days.

(21) Appl. No.: 11/805,914

(22) Filed: May 25, 2007

(65) Prior Publication Data
US 2008/0002179 A1  Jan. 3, 2008

(30) Foreign Application Priority Data
May 30, 2006 (DE) .................. 10 2006 025 005

(51) Int. Cl.
*G01N 33/48* (2006.01)
(52) U.S. Cl. .................. 356/39; 356/40; 356/41
(58) Field of Classification Search ............ 356/39–43
See application file for complete search history.

(56) References Cited

U.S. PATENT DOCUMENTS

| | | | |
|---|---|---|---|
| 3,802,776 A | 4/1974 | Tchang | |
| 3,854,878 A | 12/1974 | Kiesow | |
| 3,902,806 A | 9/1975 | Bober | |
| 4,444,498 A | 4/1984 | Heinemann | |
| 4,765,340 A | * | 8/1988 | Sakai et al. ............. 600/324 |
| 4,810,090 A | 3/1989 | Boucher et al. | |
| 4,847,910 A | * | 7/1989 | Sakuraba et al. ........... 382/134 |
| 4,925,299 A | 5/1990 | Meisberger et al. | |
| 5,315,995 A | 5/1994 | Rivers | |
| 6,080,583 A | 6/2000 | Von Bahr | |

FOREIGN PATENT DOCUMENTS

| DE | 2114064 | 10/1972 |
|---|---|---|
| DE | 2417115 | 1/1975 |
| DE | 2512561 | 10/1975 |
| DE | 3726524 | 2/1989 |
| DE | 3828618 | 3/1989 |
| DE | 19821903 | 1/1999 |
| DE | 693 30 193 T2 | 1/2002 |

* cited by examiner

*Primary Examiner*—Michael P Stafira
(74) *Attorney, Agent, or Firm*—Stuart J. Friedman

(57) ABSTRACT

A measuring cell for receiving a blood sample is designed such that it can be transilluminated with a light source. The light source and a means for determining the luminous intensity corresponding to the light source can be arranged on the measuring cell for determining the luminous intensity of the light of the light source emerging from the measuring cell, wherein the measuring cell has constant, predefined properties with respect to the light of the light source, so that the blood oxygen content of the blood sample can be detected on the means for determining the luminous intensity due to a change of the luminous intensity of the light of the light source.

2 Claims, 11 Drawing Sheets

METHOD AND APPARATUS FOR DETERMINING BLOOD OXYGEN

TECHNICAL FIELD

This invention relates to a measuring cell for determining the blood oxygen content of a blood sample. The invention also relates to a method and an apparatus for determining the blood oxygen content of a blood sample.

BACKGROUND OF THE INVENTION

The oxygen saturation measurement or also measurement of the oxygen content of blood is well known since the 1960ies as so-called pulse oximetry. This method utilizes the fact that the color of blood depends on its oxygen saturation. For the transport of oxygen in blood, hemoglobin (Hb) is responsible, which by addition of $O_2$ turns into oxyhemoglobin ($O_2$Hb). When much oxygen is bound in the blood, the same has a red shade. In the case of a lower oxygen content in blood, the color of blood changes in the direction of a blue shade. This effect is due to the optical properties of the hemoglobin molecule. An oximeter measures the color differences of blood and therefrom calculates the oxygen saturation content.

The physical basis of this measurement method is the absorption of light according to the Lambert-Beer law. This law states that the total absorption of a medium which consists of different substances is the sum of the individual absorptions. The absorption of a substance depends on its concentration, the thickness and the material constant. The material constant is the molar extinction coefficient of the substance.

When radiation of a certain intensity is passed through a medium, the intensity decreases upon passage through the absorbing medium. The substance hemoglobin, which should be analysed for determining the oxygen saturation, chiefly consists of four constituents. These are $O_2$Hb and Hb as functional fraction as well as COHb (carboxyhemoglobin) and MetHb (metahemoglobin) as dysfunctional fraction. The aforementioned constituents of hemoglobin have different absorption characteristics for light. These different absorption properties can be evaluated by means of a spectrophotometric measurement method and be used for determining the oxygen saturation. These connections are well known among experts (cf. also FIG. 1).

So-called pulse oximeters are known. These apparatuses used in the non-invasive measurement of the oxygen saturation utilize the variable strength of the absorber substance blood, i.e. the change of the distance covered by the light when passing through the absorber substance. The change in strength results from the pulse. Due to the heartbeat, a pulse wave runs through the arteries. The pulse wave generates a rhythmic expansion of the blood vessels and thus effects that for instance the finger—slightly—expands with each heartbeat. According to the Lambert-Beer law, the variable path length of the light passing through the absorber substance with a constant concentration of the blood oxygen causes a changing absorption. This change in absorption is used for determining the oxygen saturation.

One particularity of pulse oximetry consists in that during the measurement a different absorber substance or different properties of the absorber substance must be considered each time. For instance, the fingers or the ear lobes (as examples of typical measurement sites of pulse oximeters) of different people are different. Therefore, the pulse oximeter, which e.g. in the form of a clip is put onto the finger or the ear lobe, must each be adapted to the new medium. The consequence is that there must be a very great dynamic range of the measuring device coupled with the pulse oximeter. In addition to the varying individual properties of each subject, the above-described regular fluctuations occur as a result of the propagating pulse wave in the body. In conventional pulse oximetry, the fluctuations caused by the pulse wave are utilized to eliminate the individual, but constant physical properties of the persons to be measured from the measurement result. For this purpose, the rhythm of the heartbeat is extracted from the measurement signals, so that the measurements are in a defined relationship with the heartbeat. If these measured values, which are correlated in time with the pulse wave, then are subtracted, the constant part of absorption caused by the tissue then is eliminated due to the subtraction. The above explanations clearly illustrate that the pulse wave is an essential prerequisite for performing the blood oxygen measurement in connection with the pulse oximetry.

The known pulse oximeters employ light emitting diodes (LEDs) with two wavelengths for determining hemoglobin and oxyhemoglobin. The other constituents of hemoglobin are considered only rarely. In a measurement with 2 LEDs, the other light-absorbing constituents of blood are included in the measurement result merely as errors. Typically, LEDs with the wavelengths of 660 nm and 940 nm are used. If the amounts of further hemoglobin constituents should also be determined, a further light emitting diode with a specific wavelength, which corresponds to the absorption behavior of the substance to be identified, must be used for each constituent. Correspondingly, there are pulse oximeters with e.g. four or five light emitting diodes.

A conventional pulse oximeter cannot be used when the blood does not pulsate, as is already indicated by the name "pulse oximeter". The expansion of a vessel necessary for pulse oximetry does not exist in the case of a measurement of the oxygen saturation outside the human body.

It is an object of the invention to provide an oximeter which supplies reliable measurement results when the blood does not pulsate, in particular when the blood is outside the living being to be examined.

SUMMARY OF THE INVENTION

The inventive measuring cell for receiving a blood sample is designed such that it can be transilluminated by means of a light source, and the light source and a means for determining the luminous intensity corresponding to the light source can be arranged on the measuring cell for determining the luminous intensity of the light of the light source emerging from the measuring cell. With respect to the light of the light source, the measuring cell has constant, predefined properties, so that the blood oxygen content of the blood sample is detectable on the means for determining the luminous intensity due to a change in the luminous intensity of the light of the light source.

The measuring cell of the invention is provided for determining the blood oxygen content of a blood sample taken from the human body or the animal body. It is quite obvious that the pulsating expansion and contraction caused by the rhythm of the heart, which is utilized in pulse oximetry, is not present in such a blood sample. Instead, the present invention proposes to precisely define the properties of the measuring cell with respect to its influence on the luminous intensity when passing through the measuring cell, and to utilize such knowledge in the measurement. For this purpose, the measuring cell e.g. has smooth surfaces and edges on which the light source and the means for determining the luminous intensity can be arranged. The light sources usually are light emitting diodes or the like. The means for determining the luminous intensity typically is a photodiode. However, arrangements with other light sources and light measuring means, which e.g. are also based on the filtering of broadband light, are also conceivable. Since the influence of the measuring cell on the intensity of light is known, the calculation method for determining the blood oxygen content based on the measured luminous intensity can do without a pulsation of the medium. Upon calibration, future measurements at the measuring cell can be effected without further calibration steps. In the case of a correspondingly precise manufacture, the initial calibration possibly can also be omitted. In accordance with the invention, it is provided that the measuring cell either is transilluminated, so that the means for determining the luminous intensity is arranged on the opposite side of the measuring cell (transmission) or that the luminous intensity reflected back from the blood sample is determined (reflection). In the second variant, the means for determining the luminous intensity (e.g. one or more photodiodes) typically is arranged on the same side as the light source. In both cases, a plurality of photodiodes can of course be used for determining the luminous intensity, just as light emitting diodes which can emit different colors.

A preferred predefined property of the measuring cell is a predefined length of path specified by the measuring cell, which is covered by the light from the light source on its way through the measuring cell to the means for determining the luminous intensity. This is also true for the case of reflection and the case of transmission. In particular, with such a defined length of path as one of the known and well-defined properties of the measuring cell, the influence of the measuring cell on the change of the intensity of light during transillumination of the measuring cell becomes predictable. Of course, this length of path is not the only property of the measuring cell which must be defined correspondingly, but it is of great importance. Thus, if the length of path is known and if the same remains constant during the measurement, it can be concluded that a change of the luminous intensity of a suitable light source is caused by the blood oxygen content of the blood sample.

Preferably, the measuring cell includes an interior space for receiving the blood sample, which is designed such that the light of the light source on its way to the means for determining the luminous intensity through the measuring cell has a second defined length of path through the interior space. In so far, not only the outer length of path through the measuring cell, but also the length of path through the blood sample is given. This provides for a further simplification of the method.

It is preferred that the measuring cell is transparent in the visible region. In the typical applications for blood oxygen measurement, the measuring cell is made of a transparent material, in order to facilitate the penetration with light in the wavelengths of the visible light. However, variants are also conceivable, in which the material effects a filtering or a defined damping of the light. A further advantage of transparency consists in that it can be recognized from outside whether blood is present in the sample.

Preferably, the measuring cell of the invention can be coupled to supply means, such as tubes or Luer lock couplings, through which a fluid or also the blood sample can be supplied or also be discharged. This provides for introducing the blood sample into the measuring cell in a fixed arrangement. Thus, the measuring cell can be coupled e.g. with a given tube system, so that the blood can directly be transferred from the measuring system into the measuring cell by means of a suction device (syringe) or the like. Typically, a sodium chloride solution is present in the supply and discharge conduits and in the measuring cell, which is sucked off, while the blood is sucked in at the same time.

A preferred application of the measuring cell of the invention resides in the field of cardiac catheter examinations, as here a conventional pulse oximeter cannot be used. When performing a cardiac catheter diagnosis, the blood oxygen content of the blood in the vessels of the heart is of interest. This blood typically is withdrawn from the heart and examined for the blood oxygen content in an external laboratory. Such blood sample from the heart or also from the cardiac catheter is of course not suitable for pulse oxymetry. Advantageously, the measuring cell can be coupled with the cardiac catheter measuring system. Sucking the blood in and out can then be effected at certain intervals during the examination or between the examinations. With respect to this application, the measuring cell of the invention and its application have particular advantages. While it is necessary according to conventional methods to take a blood sample from the patient and examine the same for the blood oxygen content in a laboratory, the measuring cell of the invention and the use thereof by employing the methods and apparatuses of the invention as described below provide for a clear simplification. On the one hand, blood oxygen values can be determined directly on site and in so far are available to the physician for examination. On the other hand, a blood sample taken from the body for determining the blood oxygen content can be recirculated into the body during the examination. As a result, less strain is put on the body during the examination, and the examination results are available much faster. Above all, no or only very little loss of blood occurs with the measuring cell of the invention.

Preferably, the interior space of the measuring cell, which receives the blood sample, has a greater extension in a first dimension than in a second dimension. The distance to be covered preferably is the smaller dimension. To put it simply, the measuring cell has a rectangular cross-section of the interior space. In this advantageous aspect it is considered that when passing through the measuring cell and the blood sample, the beam of light tends to diverge. What is in the foreground is the fact that only as little blood as possible should be taken from the body with every examination. With a further extension in one plane and a very flat layer of blood, this aspect is taken into account.

In accordance with a further aspect of the invention, a method is provided. For determining the blood oxygen content of a blood sample, the following steps are performed: transilluminating the blood sample with light on a specified length of path and measuring the intensity of light upon covering the specified length of path. The two steps are repeated, until a sufficient number of measured values is obtained, so as to be able to calculate the blood oxygen content from the measured intensities of the light. In the method of the invention, the specification of a specified length of path also is in the foreground, which provides for omitting the pulsation of the blood sample. Preferably, the blood sample first is transilluminated with light of a first wavelength and then with light of a second wavelength, the intensity of the two beams of light being determined in each case. In accordance with the invention, these steps are repeated, until the blood oxygen content can be determined with sufficient accuracy from the measured intensities. Repetitions between one and ten times can be advantageous. Of course, other repetition rates are also conceivable.

Preferably, the process of the invention also comprises a first step for detecting blood in the path of the light. In accordance with this preferred method step, the measurement medium initially is detected. The oximeter of the invention is not used for continuously monitoring the oxygen saturation, but for a temporary measurement of the oxygen saturation, e.g. a measurement controlled by the operating personnel. This can be advantageous e.g. for use on the site of cardiac catheter measurement or in the mobile examination of athletes. Normally, no blood is present in the measuring device. If blood now is introduced into the measuring device (measuring cell), it will flow into a region where it is checked with a certain repetition rate whether blood is present in the measuring cell. Only after this check has been performed, will a regular measurement with light pulses of a specific repetition rate be initiated. In this way, energy can clearly be saved e.g. in mobile use. In the process of the invention, a measuring cell as described above preferably is used, so that the defined length of path is specified by the design of the measuring cell.

In particular when used on a site of cardiac catheter measurement, the measuring cell can be filled e.g. with sodium chloride solution, just as the tube system via which the measuring cell is coupled with the point of blood withdrawal. For examination, the sodium chloride solution then can be sucked off from the measuring cell, so that blood will flow in and finally fill the measuring cell. As far as here an automatic detection of blood is provided, a measurement can be effected as soon as the blood has reached the measuring cell. In so far, a further manual operation possibly can be omitted.

In accordance with a further aspect of the invention, an apparatus for measuring the blood oxygen content is provided. The same includes a control unit which is designed such that it can execute the method described above. For this purpose, electronic processors, memories and the like typically are required.

A way for the safe detection of the measurement medium is the use of a source of radiation with a wavelength below 600 nm. In this wavelength range, the hemoglobin fractions absorb almost completely, whereas in this wavelength range a sodium chloride solution with water as main constituent absorbs only to a very small extent. A simple and inexpensive alternative to the detection of the measurement medium can be the use of one of the two measured wavelengths present. Favorably, the source of radiation with the longer wavelength should be used for this purpose, because water in the wavelength range from 600 to 800 nm has a very low absorption. Accordingly, the LED with the shortest wavelength will be used for detecting a bloodless fluid (e.g. sodium chloride solution). It can be assumed that the sodium chloride solution hardly absorbs this wavelength. Accordingly, a great signal must be expected.

In a preferred embodiment, the apparatus of the invention also comprises a light source and a means for determining the luminous intensity, which typically is light emitting diodes and photodiodes. The source preferably is suited to emit light of two different wavelengths. However, light sources comprising more than two wavelengths, i.e. more than two light emitting diodes are also conceivable.

A particularly preferred embodiment of the apparatus of the invention provides for a wireless reception and transmission of data. For this purpose, technologies such as Bluetooth or the like typically are used. This is a technology for the wireless transmission of data or voice signals. A particular advantage of the method and the apparatus of the invention consists in that they are also suitable for mobile use; in contrast to the known pulse oxymetry, the method of the invention also provides for determining blood oxygen values distinctly below 50%. Therefore, the present invention is suitable for applications which cannot be considered for conventional pulse oxymetry. These include e.g. examinations on sites of cardiac catheter measurement or on athletes under high strain. In these applications, it is particularly advantageous when the apparatus of the invention includes its own energy supply, a wireless transmission of data, and the like.

DETAILED DESCRIPTION OF THE EMBODIMENTS

Figure 1:
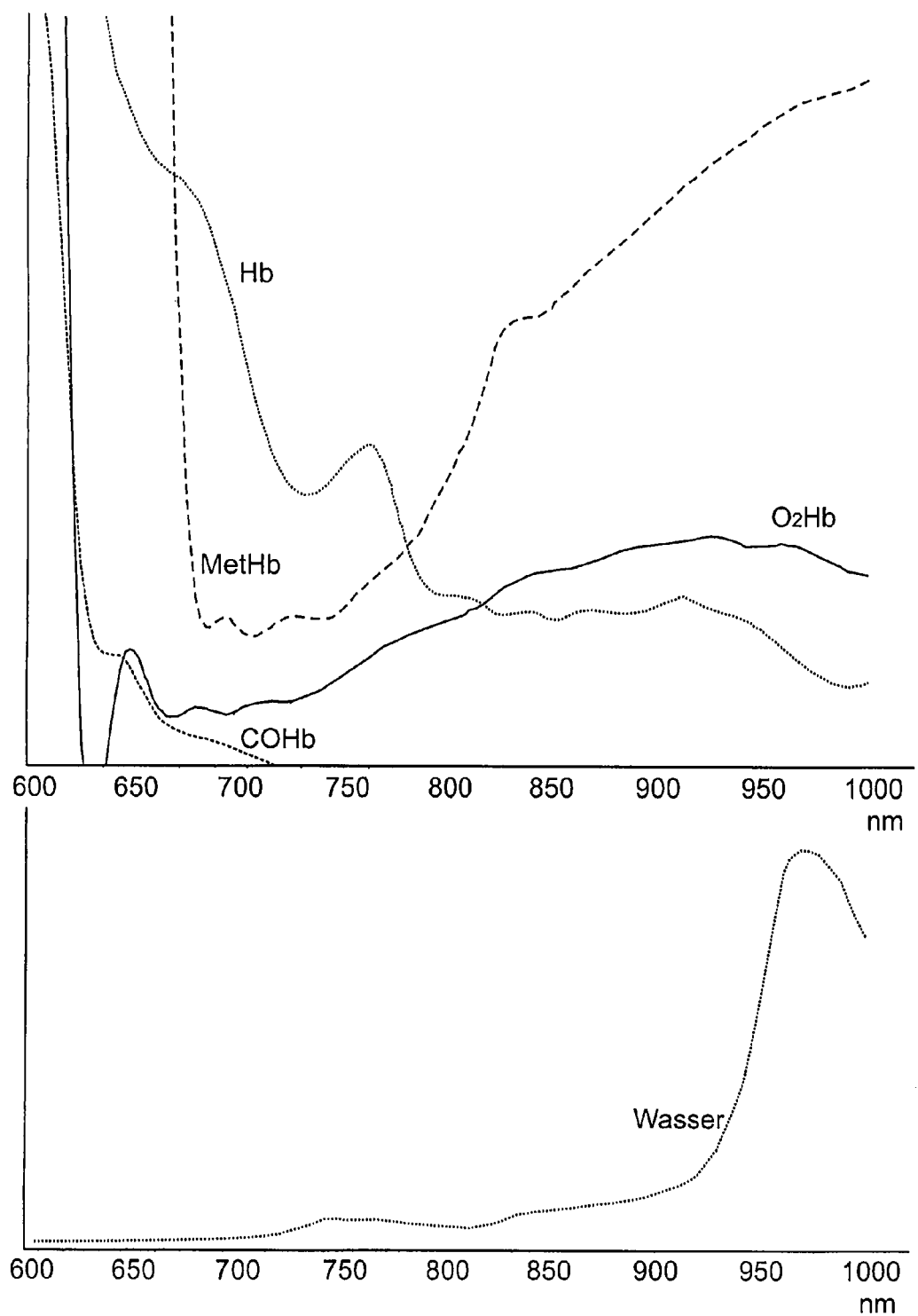
FIG. 1 shows representations of the light absorption behavior of the four most important hemoglobin constituents Hb, $O_2Hb$, MetHb and COHb, and among these the light absorption behavior of water.

In its upper half, FIG. 1 qualitatively shows the absorption spectrum of hemoglobin (Hb), oxyhemoglobin ($O_2Hb$), carboxyhemoglobin (COHb), and methemoglobin (MetHb) in a wavelength range from 600 nm to 1000 nm. The absorption spectrum reveals that a suitable wavelength for determining the blood oxygen content is about 660 nm, because here the difference of the absorptions of Hb and $O_2Hb$ reaches a high value. For the other constituents, other wavelengths preferably should be used in addition. In the lower half, a separate diagram illustrates the absorption behavior of light in water in dependence on the wavelengths of light. It can be seen that water hardly absorbs light in a range below 700 nm. This effect can be utilized to detect whether an absorber medium is present in the path of light.

Figure 2:
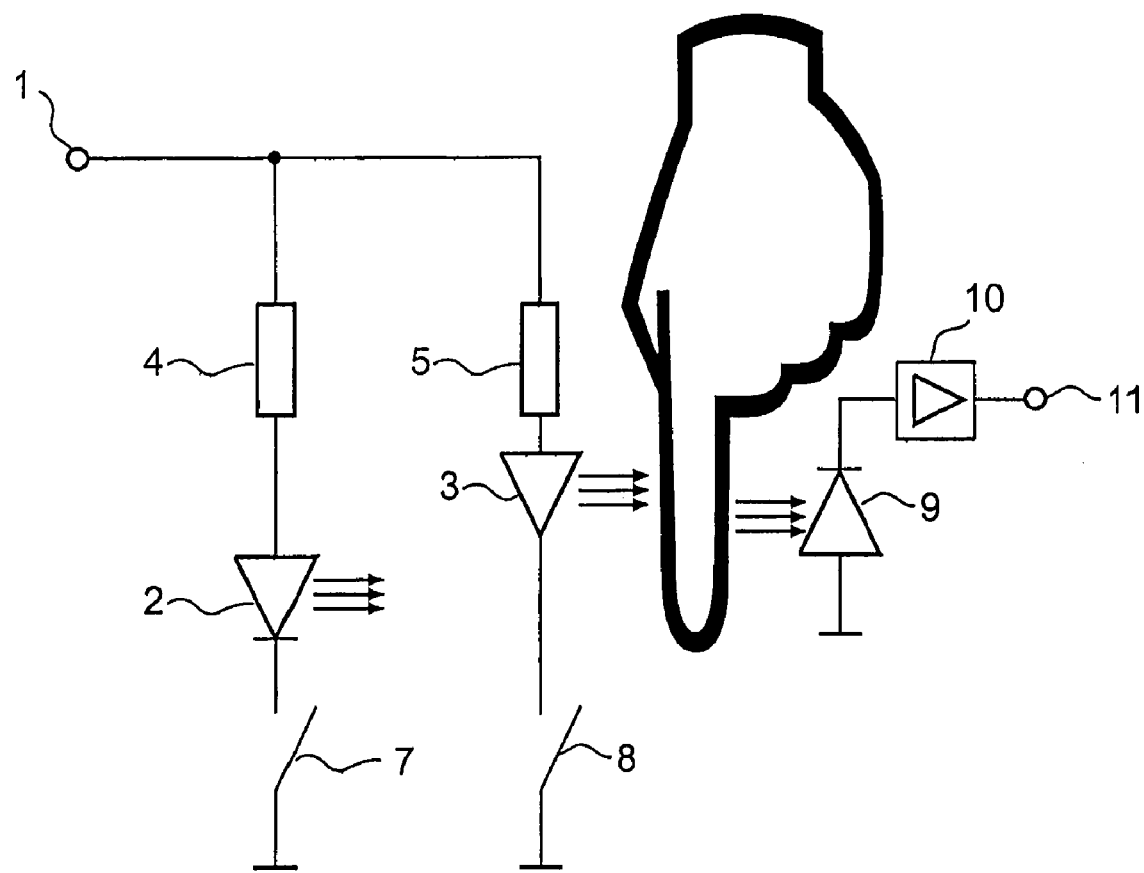
FIG. 2 shows the schematic representation of the basic structure of a measurement arrangement as it is used for pulse oxymetry in accordance with the prior art.

FIG. 2 shows a simplified, schematic representation of an arrangement for determining the blood oxygen content. The arrangement as shown in FIG. 2 is used for conventional pulse oxymetry. Similar components can, however, also be designed and controlled such that they are suitable for the method in accordance with the present invention. FIG. 2 shows a terminal 1 for applying a supply voltage, which is each coupled with a first light emitting diode 2 and a second light emitting diode 3 via two resistors 4, 5. In the paths of the light emitting diodes 2, 3 there is each disposed a switch 7 and a switch 8 for interrupting the electrical paths. The switches 7 and 8 are actuated by a non-illustrated electronics such that the light emitting diodes 2, 3 are switched on and off in regular pulses and for instance alternatingly. A non-alternating operation with two photodiodes 9 is of course also conceivable. The light emitting diodes emit light of a specific wavelength. The light emitting diode 2 for instance emits light with a wavelength of 660 nm and the light emitting diode 3 light with a wavelength of 940 nm. The light of different wavelengths, which is alternately emitted by the light emitting diodes 2, 3, penetrates through the medium 6 and impinges on the photodiode 9. The same generates a current in proportion to the impinging light, which in the amplifier 10 is postamplified and converted into a voltage proportional to the current, which voltage then is present at the output 11 of the measurement arrangement. The signal at the output 11 of the measurement arrangement is processed by a method as will be described later with reference to FIG. 5 and FIG. 6. The blood oxygen content of the blood contained in the medium 6 will be determined from the output signal 11 of the measurement arrangement.

Figure 3:
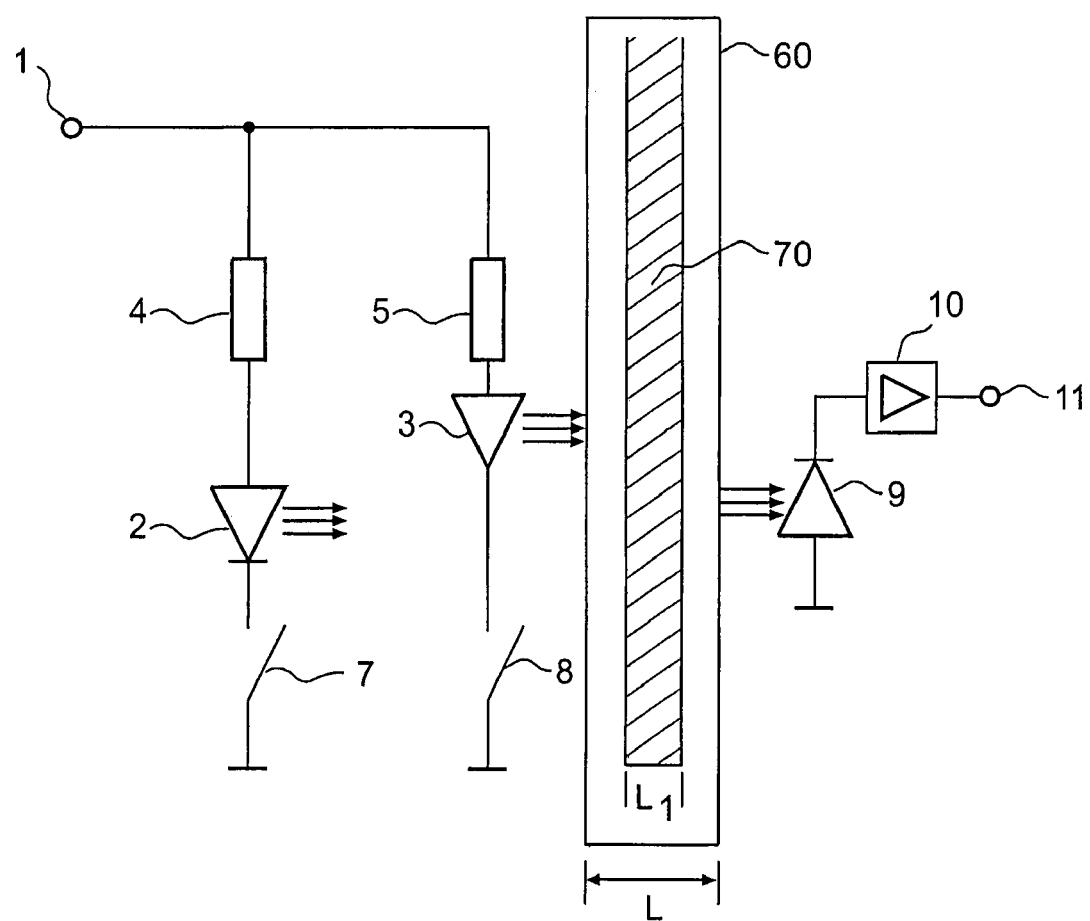
FIG. 3 shows the arrangement of FIG. 2 with a measuring cell of the invention for executing the method of the invention in a first arrangement.

FIG. 3 now shows the same arrangement as explained with reference to FIG. 2, wherein a measuring cell 60 in accordance with the teaching of the present invention now is used in accordance with the invention instead of the finger 6. The measuring cell 60 is characterized by a precisely defined path length L, which ultimately specifies the distance of the light emitting diodes 2, 3 and the photodiode 9. In general, the arrangement and also the specified path length L of the measuring cell thus provide a defined path of absorption. In accordance with the inventive measurement method for determining the blood oxygen content, a defined quantity of blood (blood sample) withdrawn from the human body is filled into the measuring cell 60. As now the blood no longer pulsates, the dimension of the measuring cell 60, in particular the path length L to be covered by the light when transilluminating the blood 70, is defined precisely. In addition, the other properties of the measuring cell are also known, which have an influence on the light, in particular the intensity of the light emitting diodes 2, 3, when the light passes through the measuring cell 60. As a result, the method and the apparatus of the invention also can do without pulsation of the absorber medium blood 70. Possibly, a single or also a repeated calibration of the measuring device is required. The chamber for the absorber medium 70 likewise has a defined length L1. In this way, the path length L1 and the path length L provide well-defined conditions for the measurement in accordance with the invention.

Figure 4:
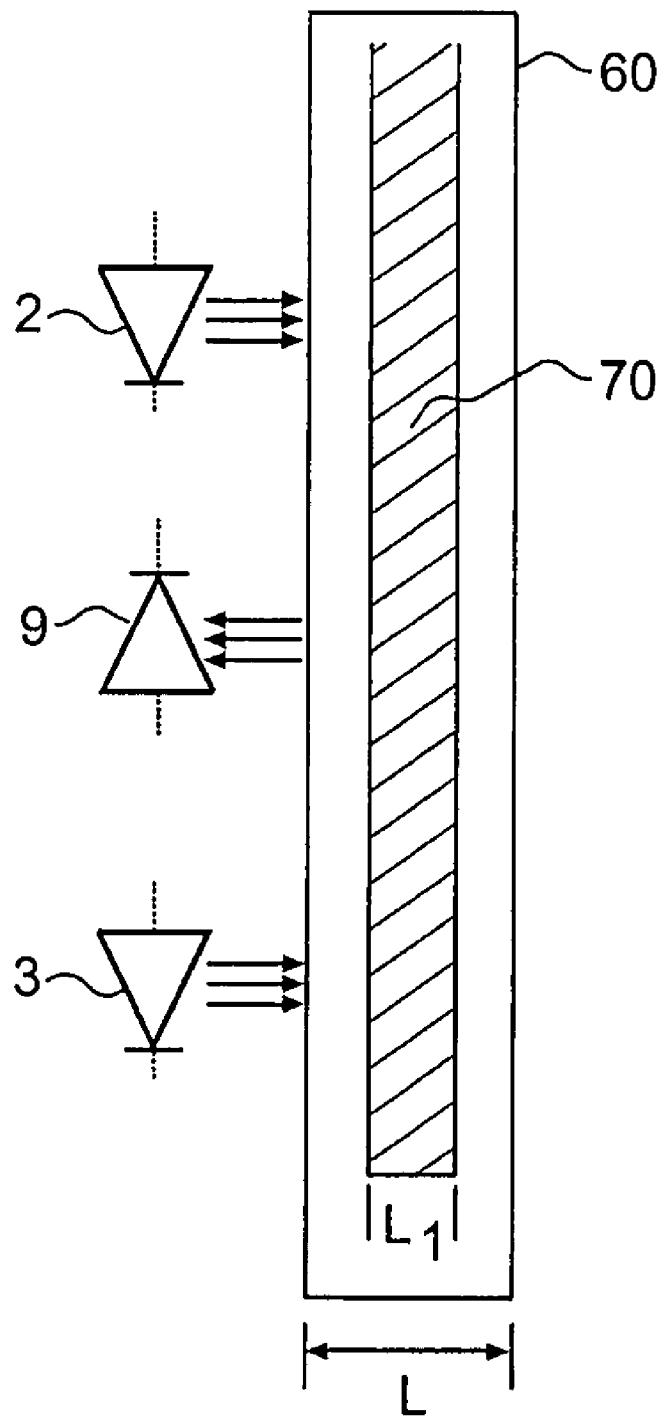
FIG. 4 shows the arrangement of FIG. 3 with a measuring cell of the invention for executing the method of the invention in a second arrangement.

FIG. 4 shows a further embodiment of the invention in a simplified form, which has the same function as the arrangement of FIG. 3, but this time the light emitting diodes 2, 3 and the photodiode 9 are in an arrangement which provides for a measurement in reflection. The light of the light emitting diodes 2, 3 is not measured on the side opposite the photodiode 9 upon passage through the measuring cell, but the reflected part is measured on the same side as the light emitting diodes 2, 3. The reflected part also depends on the blood oxygen content of the blood. Likewise, as described with reference to FIG. 3, the predetermined properties of the measuring cell on the path along which the light passes through the measuring cell are known and predefined here as well. As a result, the blood oxygen content of the blood sample can be determined in the same way as described above. Hence it follows that the invention is equally suited both for transmission and for reflection. The further components shown in FIG. 3, such as switches 7, 8, voltage source 1 or the resistors 4, 5 are omitted in FIG. 4 for simplification.

Figure 5:
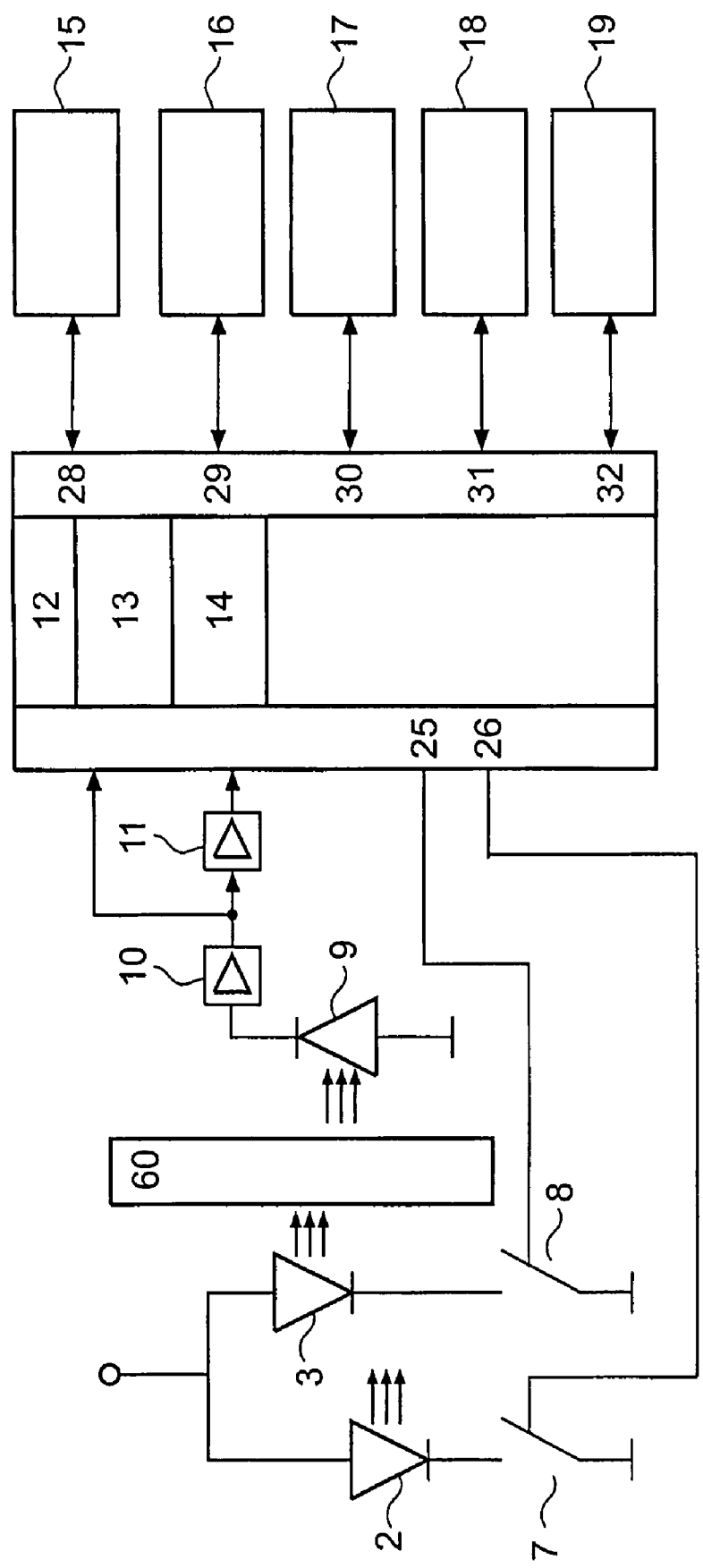
FIG. 5 shows a schematic representation of an apparatus in accordance with one embodiment of the present invention.

FIG. 5 shows the apparatus of the invention in a simplified schematic representation in accordance with FIG. 3, and in addition the control electronics and further peripheral devices are considered here in accordance with the invention. Likewise, an arrangement as shown in FIG. 4 is considered for the light emitting diodes 2, 3 and the photodiode 9. First of all, the light emitting diodes 2, 3 and the switches 7 and 8 for periodically switching on and off the light emitting diodes 2, 3 are shown here again. As described above, the light of the light emitting diodes 2, 3 with different wavelengths each falls through the measuring cell 60 onto the photodiode 9. The output signal of the photodiode is amplified in the amplifiers 10 and 11 and processed in a microprocessor 12. Typically, the output signal initially is converted from an analog into a digital value. The microprocessor 12 typically contains a program memory 13 and a data memory 14. In addition, the microprocessor 12 includes various control inputs and outputs, such as the outputs 25 and 26 for actuating the switches 7 and 8 for the light emitting diodes 2, 3. Optionally, a further output 28 can be provided on the microprocessor 12, which is provided for actuating a measurement display 15, in particular an LCD display. Another output 29 is provided for actuating a Bluetooth interface 16 or the like, via which the measured data or also control signals can be transmitted and received. Another output 30 of the microprocessor 12 in turn can be coupled with a programming interface 17, which can be used for programming the microprocessor 12. Yet another output 31 of the microprocessor 12 can be coupled e.g. with a piezoelectric signal generator 18 or the like, which in the case of certain events emits an acoustic signal. This can for instance be the case when the measured values lie outside specified ranges. A further connection 32 of the microprocessor 12 can be coupled with a voltage supply, in particular with accumulators or solar cells 19.

In accordance with the invention, the measured values of the blood oxygen also can be transmitted wireless. The present invention is particularly useful for mobile applications. This is due to the fact that the method and the apparatus of the invention can be operated in a very power-saving way. In accordance with the invention it is provided, for instance, that the light emitting diodes only are switched on for a measurement when it has previously been detected that a measurement medium (e.g. blood 70) is present in the measuring cell 60.

Another important advantage of the present invention consists in that blood oxygen values can be determined down to 40% or even 30%. The commonly used pulse oximeters usually can detect the oxygen saturation only in a range between 95% and 99%. The present invention provides for applications in which oxygen saturations of below 50% must be detected. This chiefly concerns the monitoring of athletes, e.g. during the training phase, but also the examination of the coronary vessels on a so-called cardiac catheter measurement site. In both cases, either deliberately caused or physiologically caused very low blood oxygen values occur. In particular in the case of athletes, the apparatus of the invention can be mounted directly near the body, can determine the measured values—in particular automatically—and communicate the same wireless to an evaluation unit.

Figure 6:
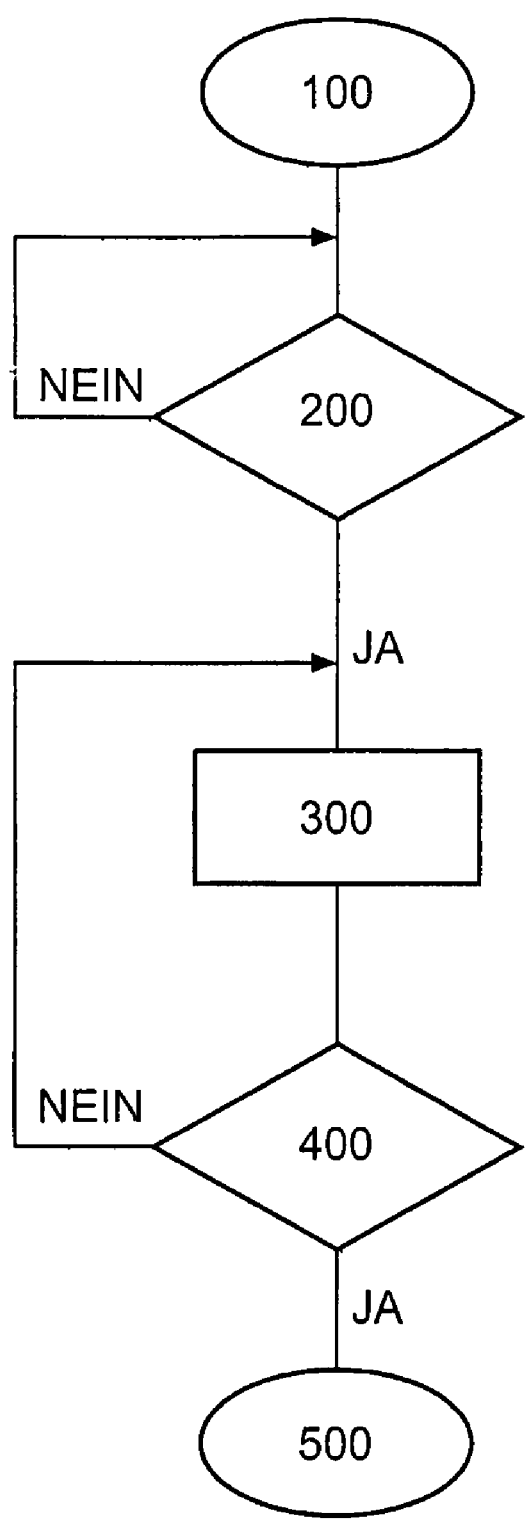
FIG. 6 shows a flow diagram which illustrates the essential steps of the method of the invention.

FIG. 6 shows a simplified flow diagram which should illustrate the sequence of the method of the invention for determining the blood oxygen content. After the method is started at position 100, e.g. by pressing a button or by inserting the measuring cell in the measuring device of the invention, it is checked first of all whether the desired absorber medium, in the present case the blood 70, is present in the measuring cell 60. This check takes place in block 200. As long as no blood 70 is present in the measuring cell 60, no measurement is started. The check in block 200 is effected e.g. by emitting light of a certain wavelength and by checking in what intensity this light arrives at the photodiode 9 of FIG. 3. As long as the light gets through the measuring cell 60 almost unchanged, no blood 70 is present there.

To be particularly power-saving, the check for the presence of the measurement medium can be effected at large intervals. But as soon as blood 70 arrives in the measuring cell 60, a measurement is started with the routine 300. Correspondingly, the light emitting diodes 2, 3 are alternately caused to glow by means of the switches 7, 8, and the measurement signal is received at the photodiode 9. Upon completion of a measurement cycle in the routine 300, which will be explained in detail below, a general control takes place in the routine 400, as to whether the measurement results lie within certain tolerances. If the control is successful, the measurement is terminated first of all. If the check in routine 400 reveals that the measurement results are useless, the measurement will be restarted in routine 300. The routine is terminated at position 500.

Figure 7:
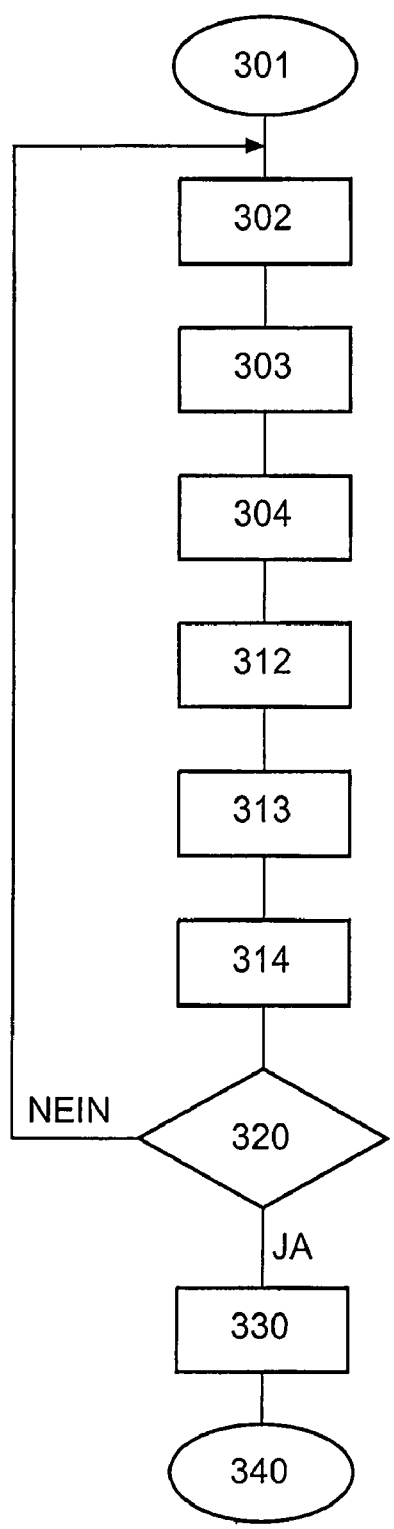
FIG. 7 shows a flow diagram for the measurement routine in accordance with the present invention.

FIG. 7 shows the flow diagram in simplified form for the routine 300 as shown in FIG. 6. After the routine 300 is started in block 301, the first light emitting diode 2 is switched on for a defined pulse duration in block 302. After the pulse is terminated, a zero adjustment is performed for the first light emitting diode in routine 303. From the measured value recorded during the light pulse of the first light emitting diode 2 a further measured value is subtracted, which is detected at the photodiode 9 directly upon switching off the light emitting diode. This eliminates the influence of extraneous light. In step 304, the measured value then is stored. The same procedure then is performed with the second light emitting diode 3 in blocks 312 (pulsation of the light emitting diode), 313 (zero adjustment), and 314 (store measured value). The procedures in accordance with blocks 302 to 314 are executed, until a certain number of repetitions is reached. Checking the number of repetitions for the measurement is effected in block 320. If the required number of repetitions is reached, the routine is executed in block 330. In this way, ten measured values can for instance be determined for each light emitting diode. As soon as the ten measured values are recorded and stored, an average over the measured values of the respective light emitting diode 2, 3 is formed in block 330, and from these two mean values the final measurement result is calculated.

In step 340, the sub-routine returns to the main routine shown in FIG. 6, where it continues with block 400.

Figure 8:
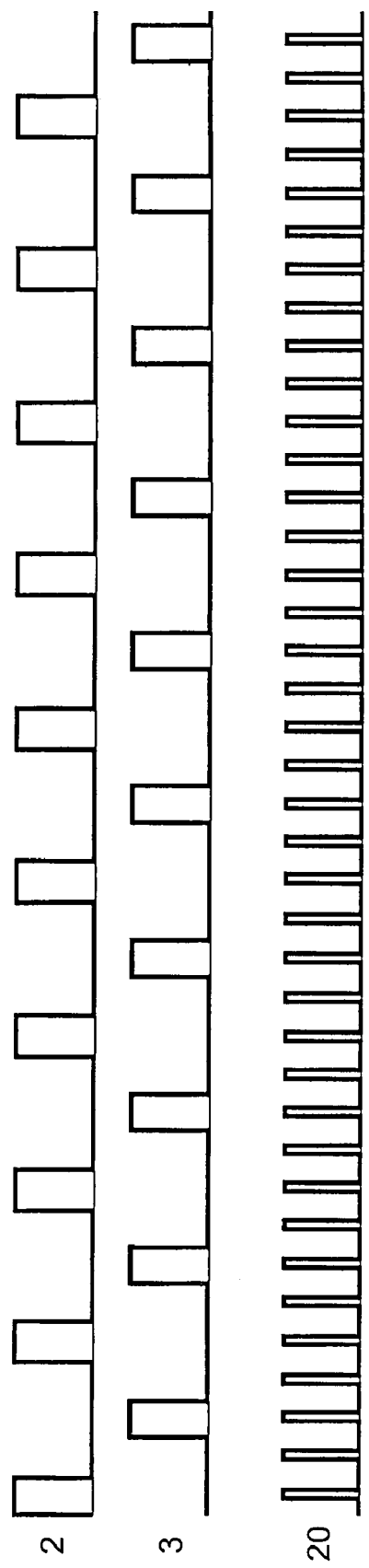
FIG. 8 shows a typical time sequence of light pulses on the light emitting diodes and the time-correlated detection of measured values in accordance with the present invention.

FIG. 8 shows a typical sequence of light pulses of the light emitting diodes 2, 3 of the measuring device of the invention when executing the method of the invention. In the line with the reference numeral 20 for an analog-digital converter, FIG. 8 also shows the times at which the measured values are detected at the photodiode 9. Thus, one measured value each is detected within the light pulse of the light emitting diode 2, and thereafter a second one at a time when none of the two light emitting diodes is switched on. Then, a measured value is detected when the light emitting diode 3 is switched on, and right thereafter, when none of the two light emitting diodes 2 or 3 emits light. The measured values recorded directly after the respective pulses of the light emitting diodes serve the above-described zero adjustment. The detection of the measured values typically is effected by an analog-digital converter 20.

Figure 9:
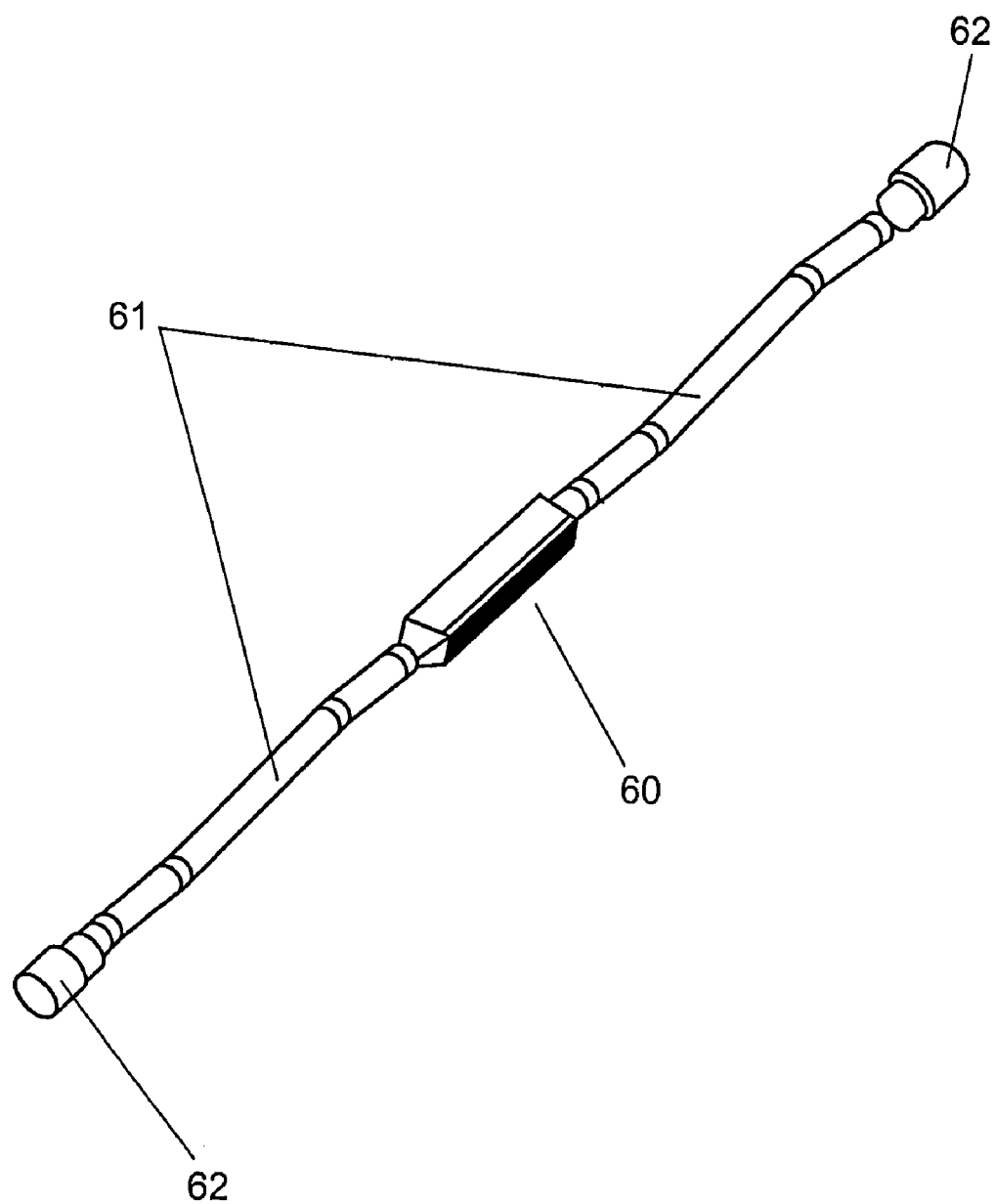
FIG. 9 shows a perspective representation of a measuring cell of the invention with connecting pieces, FIG. 10 again shows the measuring cell of the invention in a more detailed perspective representation.

FIG. 9 shows a measuring cell 60 with connecting pieces 61 and connectors 62 in a perspective, simplified representation. In accordance with the present invention, the measurement medium, e.g. blood 70, is drawn into the measuring cell 60 via the tubes. In the tubes 61 and the connectors 62 there is usually a sodium chloride solution which is sucked off on the one side, so that blood can flow in from the other side, which is coupled with a blood vessel. As soon as the measuring cell or the interior space of the measuring cell is filled with blood, a measurement is initiated either manually or automatically. As described above, the measuring cell 60 is coupled with the light emitting diodes and the photodiode. The tubes are e.g. biocompatible and transparent tubes with a bending strength according to DIN EN 13868. Due to a very small inside diameter of the tubes, the loss of blood during the examination can be minimized.

FIG. 10 again shows the measuring cell 60 in an enlarged perspective representation. In particular, the measuring chamber 700 is indicated here in broken lines in the interior space of the measuring cell 60. The dimensions of the measuring cell 60 of the invention, in particular the dimensions of the measuring chamber 700 are defined precisely, in order to maintain the specified path length L when light passes through the chamber. In accordance with the invention, the blood measuring device is calibrated for a specific measuring cell.

Figure 11:
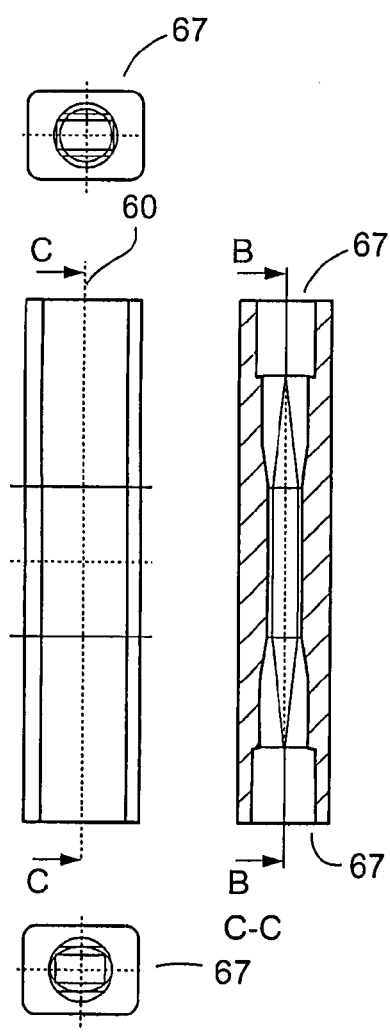
FIG. 11 shows the blood measuring cell of the invention in a top view and further representations from the front, from behind, and a section.

FIG. 11 again shows the measuring cell 60 in a top view and in a section through the measuring cell along line C-C. In addition, a front view and a rear view of the connection side 67 are shown. The interior cavity of the measuring cell 60 is designed such that rather no blood residues are left in the measuring chamber 700 or in other regions of the measuring cell 60.

Figure 10:
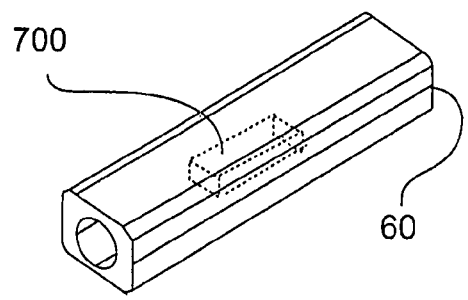
Figure 12:
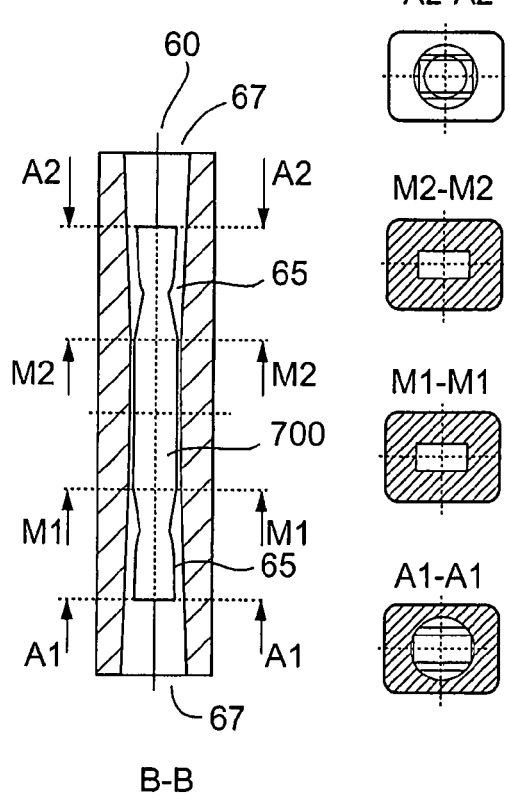
FIG. 12 shows a further sectional representation of the blood measuring cell of the invention and further sectional representations.

FIG. 12 shows a further section through the measuring cell of the invention as shown in FIG. 10 along line B-B. In addition, further sections are shown along lines A2-A2, M2-M2, M1-M1 and A1-A1. It can be seen here that the measuring chamber 700 has a rectangular cross-section. Other cross-sections are, however, also conceivable. In addition, the measuring cell of the invention includes outer connecting regions 67, filling regions 65 and the above-mentioned measuring chamber 700. It equally applies both to the measuring chamber and to the supply tubes that the inner cavity should be chosen such that as little blood as possible should be taken during the measurement.

Figure 13:
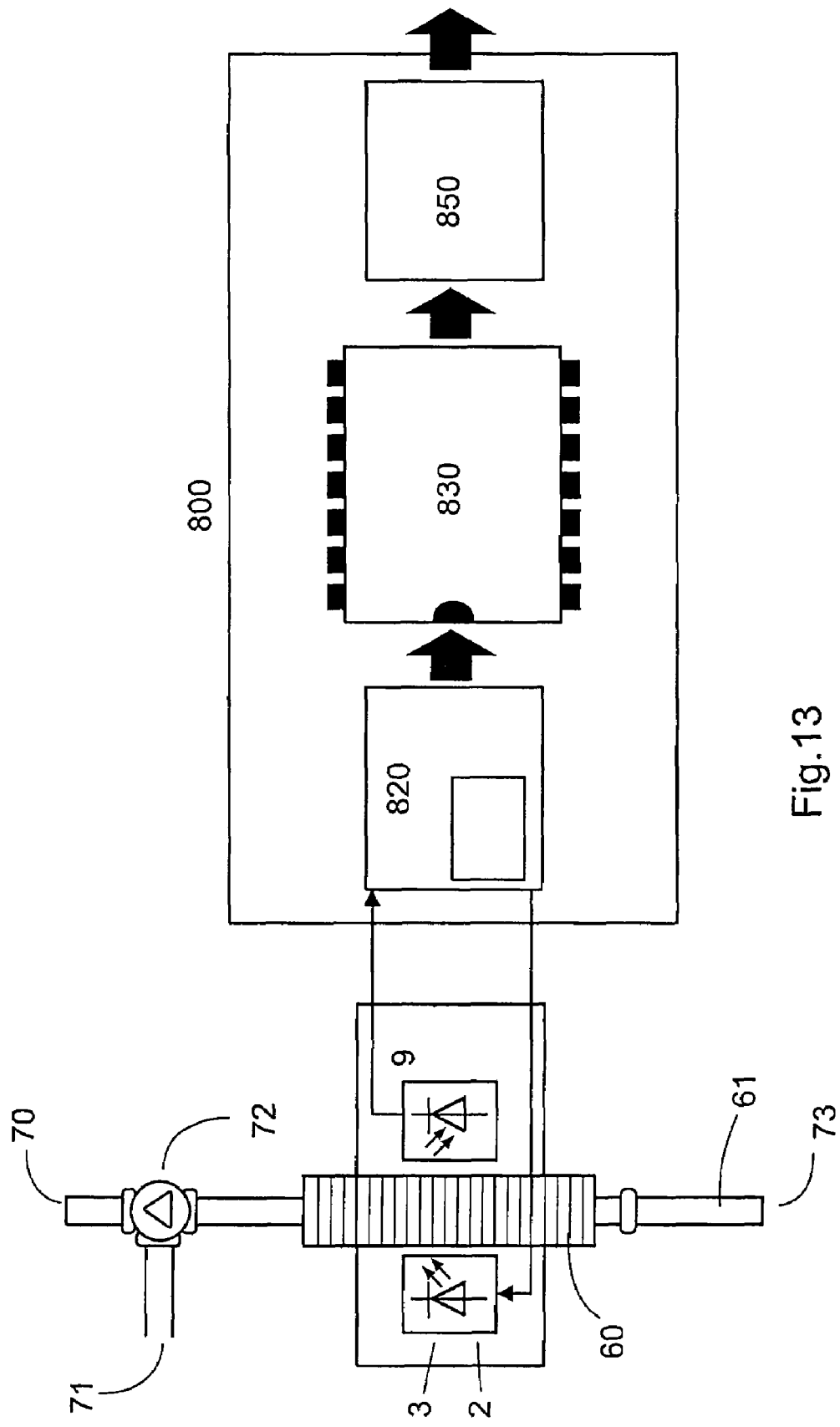
FIG. 13 shows a schematic representation of an apparatus of the invention.

FIG. 13 shows a preferred aspect of the measuring device of the invention. The measuring cell 60 is coupled with the blood or infusion stream via the supply tubes 61 and a valve 72. An infusion thus can be connected e.g. at the tube 70. A syringe might e.g. be connected via the connection 71. At the lower end 73, there is a possibility for coupling a blood vessel via further tubes. Usually, the connections are provided via so-called Luer lock connections. Around the measuring cell 60, the sensor module is disposed, which comprises the light emitting diodes 3, 4 and the photodiode 9. FIG. 13 shows an arrangement in transmission of the measuring cell 60. Nevertheless, there is also provided an arrangement in reflection for the diodes as shown in FIG. 4. Said diodes are operated by the control unit 800 according to the method described above, and the measurement signals are evaluated. Correspondingly, the control unit 800 includes a sensor unit 820 and a driver for the light emitting diodes, which triggers the pulses of the light emitting diodes 2, 3. The signal evaluation or also the averaging of the measured values is effected in the electric circuit 830. The control unit 800 likewise includes a module 850, which can effect a wireless transmission of the data to a receiving station. This module preferably is a Bluetooth module or the like.

The present invention by no means is restricted to the measuring cell of the invention, the apparatus of the invention for using the measuring cell and the methods of using the measuring cell. Rather, an essential gist of the invention also consists in the knowledge that the method of the invention and the apparatuses of the invention, in particular the measuring cell, can particularly advantageously be employed in specific applications. This applies in particular to the cardiac catheter examination. In accordance with the invention, it was recognized that it constitutes a great disadvantage that during the critical examination on the heart on a site of cardiac catheter measurement the blood oxygen values must be determined in a complicated and time-consuming way. Conventionally, a blood sample is withdrawn, forwarded to a laboratory and examined there for its blood oxygen content according to a specific examination method. When the value has been determined, the same is communicated to the physician. It is quite obvious that much time gets lost in the process. In addition, blood is continuously withdrawn from the body, which leads to an undesired loss of blood.

The use of the method of the invention and of the apparatuses described in this application now provides for a completely novel and substantially improved examination of the blood oxygen values. In accordance with the invention, the above-described measuring cell is coupled with a catheter located in the heart via a tube system or the like. The measuring cell and the tube system initially are filled with a sodium chloride solution or the like. During the examination, the sodium chloride solution is sucked off from the measuring cell and from the tube system from time to time, so that blood is transferred via the cardiac catheter from the position of interest on the heart into the measuring cell. As soon as the measuring cell is filled with blood, the examination of the blood oxygen value can be effected automatically or upon request. However, an automatic start of the measurement is preferred. Since the blood is not influenced during the examination, it can be recirculated into the body after the examination by merely washing up sodium chloride solution from the other side of the measuring cell, so that the blood is recirculated to that point of the heart where it was withdrawn.

The blood oxygen measurement in accordance with the present invention by using the apparatuses of the invention and the measuring cell of the invention can be used particularly advantageously in cardiac catheter diagnosis. There are considered in particular angiocardiography, i.e. the representation of the cardiac cavities and vessels close to the heart by contrast media, the determination of the cardiac output according to Dr. Fick or other methods, the determination of the vascular resistances, the shunt diagnosis, the probing in a child's heart and left/right heart probings with adults. The method also can be used very advantageously in intensive monitoring. For instance, when monitoring respiration or when monitoring the cardiac output. In particular, the invention is advantageous in oxygen therapy, i.e. in the control of the success of a therapy. This is likewise true for ergospirometry, i.e. the control of the performance of the lungs. Briefly, the present invention can advantageously be used in all fields in which blood oxygen measurement is of great importance.

The invention claimed is:

1. An apparatus for determining the blood oxygen content of a blood sample in connection with a cardiac catheter examination, wherein a catheter is located in a position of interest in the heart, the apparatus being coupled with a cardiac catheter measuring system, said apparatus comprising:

a measuring cell for receiving a blood sample which can be transilluminated with a light source, said light source and a means for determining the luminous intensity corresponding to said light source are arranged on said measuring cell for determining the luminous intensity of the light of said light source emerging from said measuring cell, said measuring cell having constant, predefined properties with respect to the light of said light source, whereby the blood oxygen content of the blood sample can be detected due to a change of the luminous intensity of the light of said light source on said means for determining the luminous intensity;

a suction device and a tube system for sucking off a sodium chloride solution from said measuring cell, said tube system being coupled with the catheter located in a position of interest in the heart, whereby a blood sample can be received in said measuring cell;

a control unit for automatically performing a specified measurement routine during operation, in which said measuring cell is transilluminated with light on a specified length of path, the intensity of the light is measured upon transillumination, the presence of blood in said measuring cell is detected based on the measured intensity of the light, a measurement of the blood oxygen content of the blood sample in said measuring cell by transillumination of said measuring cell is started and performed if the presence of blood has been detected in the previous step, whereby blood oxygen values below 50% blood oxygen saturation can be determined, and sodium chloride solution is introduced into said measuring cell by means of said suction device to remove the blood sample from said measuring cell and to recirculate the blood to the position of interest in the heart from which it was withdrawn.

2. An apparatus, as claimed in claim 1, wherein said light source is suitable for emitting light of two different wavelengths.

* * * * *